(12) United States Patent
Stauffer

(10) Patent No.: US 7,365,233 B2
(45) Date of Patent: Apr. 29, 2008

(54) METHYL MERCAPTAN PROCESS

(76) Inventor: John E. Stauffer, 6 Pecksland Rd., Greenwich, CT (US) 06830

( * ) Notice: Subject to any disclaimer, the term of this patent is extended or adjusted under 35 U.S.C. 154(b) by 66 days.

(21) Appl. No.: 11/443,983

(22) Filed: May 31, 2006

(65) Prior Publication Data

US 2007/0282131 A1    Dec. 6, 2007

(51) Int. Cl.
*C07C 319/00*    (2006.01)
(52) U.S. Cl. .................................................. 568/70
(58) Field of Classification Search ............... 568/70
See application file for complete search history.

(56) References Cited

U.S. PATENT DOCUMENTS 4,410,731 A * 10/1983 Buchholz ................... 568/70
4,449,006 A * 5/1984 Haines ....................... 568/70
4,544,649 A * 10/1985 Wachs et al. ............... 502/350
4,570,020 A * 2/1986 Ratcliffe et al. ............ 568/70
4,665,242 A * 5/1987 Boulinguiez et al. ........ 568/70

OTHER PUBLICATIONS

Conant, J.B. and A. H. Blatt, "The Chemistry of Organic Compounds," 3rd ed., The MacMillan Co., New York, 1947, pp. 342-343.
Kirk-Othmer, "Encyclopedia of Chemical Technology," 4th Ed., Wiley & Sons, vol. 16, pp. 539-541; vol. 19, p. 368; vol. 24, p. 23.

* cited by examiner

*Primary Examiner*—J. Parsa
(74) *Attorney, Agent, or Firm*—Young Basile

(57) ABSTRACT

A process is provide for the production of methyl mercaptan from synthesis gas and hydrogen sulfide. The process comprises the reaction of carbon monoxide with hydrogen and hydrogen sulfide to produce methyl mercaptan and carbon dioxide. The reaction is carried out in the gas phase over a solid catalyst.

3 Claims, 2 Drawing Sheets

METHYL MERCAPTAN PROCESS

FIELD OF THE INVENTION

The present invention relates to a process for the manufacture of methyl mercaptan, also known as methanethiol. In the process, carbon monoxide, hydrogen, and hydrogen sulfide are reacted in the presence of a catalyst to produce methyl mercaptan and carbon dioxide. The required carbon monoxide and hydrogen may be supplied by synthesis gas.

BACKGROUND OF THE INVENTION

The common method of preparing methyl mercaptan on an industrial scale is by passing vapors of methyl alcohol or methanol and hydrogen sulfide over a catalyst at elevated temperatures to produce methyl mercaptan and water. This method is direct and produces relatively high yields of product.

The principal disadvantage of using alcohol substitution to produce methyl mercaptan is the cost of the raw material, methanol. This alcohol must be produced from synthesis gas in a high pressure process. Although readily available in commerce, methanol is subject to wide price movements.

Therefore, an object of the present invention is to provide a process for methyl mercaptan that is independent of methanol. Furthermore, it is a goal of the process to achieve high conversions under mild operating conditions. These and other objects, features and advantages will be apparent from the following description.

SUMMARY OF THE INVENTION

In one particular embodiment of the present invention, carbon monoxide, hydrogen, and hydrogen sulfide are reacted over a catalyst in a reactor to give methyl mercaptan and carbon dioxide. The stoichiometry of the reaction requires two mols of carbon monoxide for each mol of hydrogen and each mol of hydrogen sulfide.

The catalyst composition for the reaction may vary considerably depending on operating conditions. A preferred composition, however, comprises thorium oxide. In addition, the catalyst may comprise zinc-chromium oxide or palladium.

Operating conditions are dictated by thermodynamic considerations and by reaction kinetics. The favored temperature for the reaction is in the range of 250° C. to 350° C. but may extend to higher or lower temperatures. The operating pressure is in the range of 1 to 10 atmospheres but again should not be limited by these constraints.

Methyl mercaptan product is most conveniently recovered by refrigeration. Any unreacted hydrogen sulfide can be removed by scrubbing the exit gas stream from the reactor with an alkanolamine solution.

DETAILED DESCRIPTION OF THE PROCESS

The present invention comprises the reaction of carbon monoxide (CO), hydrogen ($H_2$) and hydrogen sulfide ($H_2S$) over a catalyst to give methyl mercaptan ($CH_3SH$) and carbon dioxide ($CO_2$) according to the following equation:

$$2CO + H_2 + H_2S \rightarrow CH_3SH + CO_2 \qquad 1.$$

If an excess of hydrogen is used in the process, a side reaction is possible whereby some water ($H_2O$) is formed as follows:

$$CO + 2H_2 + H_2S \rightarrow CH_3SH + H_2O \qquad 2.$$

Figure 1:
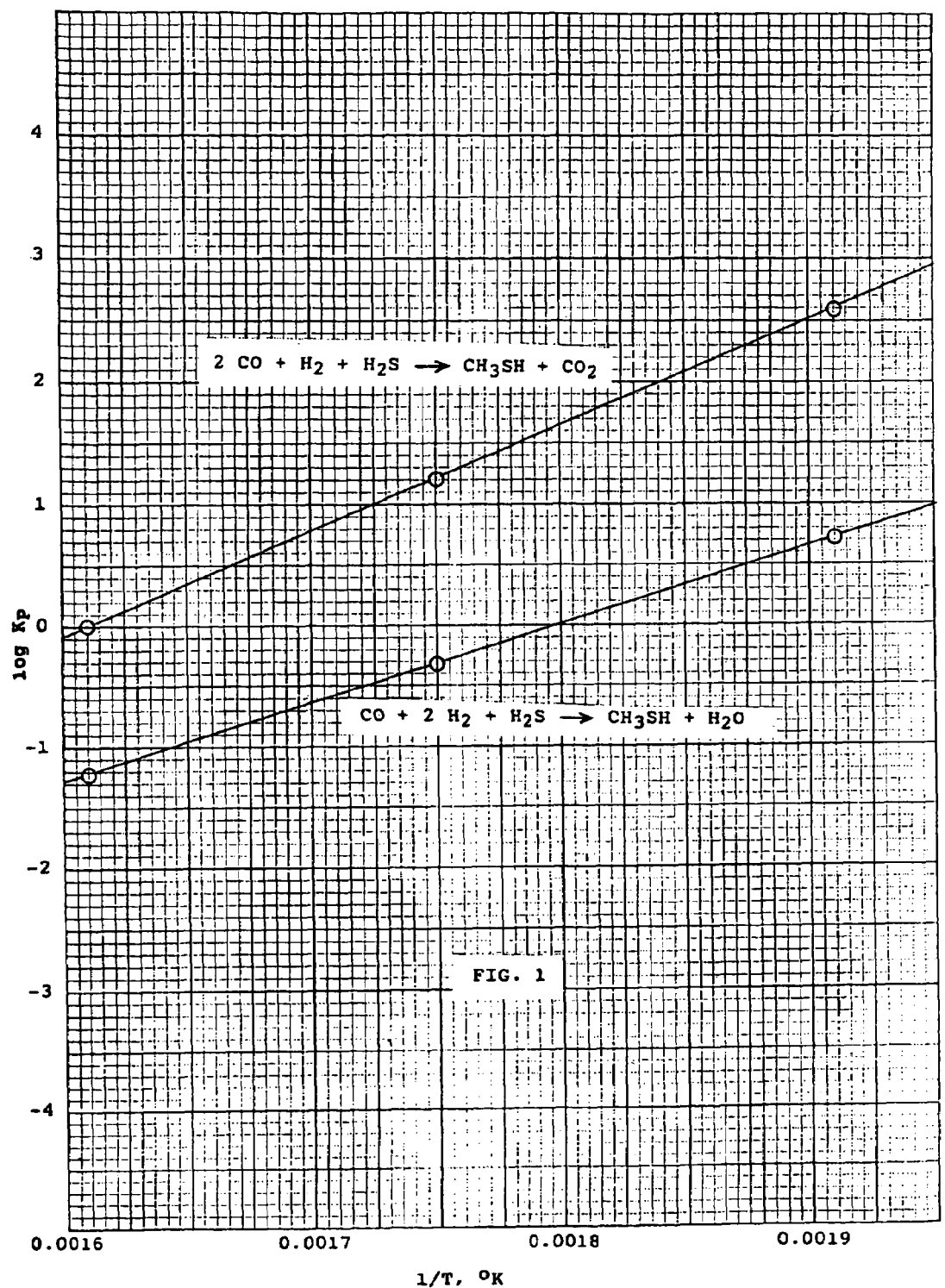
FIG. 1 is a graph showing the equilibrium conversions for the reaction of the present invention. Moreover, the results are shown for a side reaction in which water is produced.

The preferred reaction is the one shown by equation 1 whereby the process is maintained under anhydrous conditions. Besides, thermodynamic data are more favorable for reaction 1. The results are shown in FIG. 1 in which the logarithm of the equilibrium constant $K_p$ is plotted against the reciprocal of the absolute temperature T for both reaction 1 and 2. Under equilibrium conditions, higher conversions are achieved at all temperatures for the reaction of equation 1.

An important consideration of the present invention is the nature of the catalyst. The reaction kinetics requires the use of a catalyst. In the absence of experimental data, the composition of the catalyst must be determined from a theoretical analysis. This was accomplished by postulating a mechanism for the reaction.

The most plausible mechanism for the reaction is illustrated by the following equations:

$$2CO + 4H_2 \rightarrow 2CH_3OH \qquad 3.$$

$$CH_3OH + H_2S \rightarrow CH_3SH + H_2O \qquad 4.$$

$$CH_3OH + H_2O \rightarrow CO_2 + 3H_2 \qquad 5.$$

Combining equations 3, 4, and 5, one obtains equation 1. This mechanism shows that methanol ($CH_3OH$) is first produced from carbon monoxide and hydrogen. This alcohol is then combined with hydrogen sulfide to form methyl mercaptan and water. The water reacts with additional methanol to give carbon dioxide and hydrogen.

Equation 3 represents the well-known reaction for methanol synthesis. It is catalyzed by a zinc-chromium oxide catalyst or by the more active copper-zinc-alumia catalyst. (Kirk-Other, *Encyclopedia of Chemical Technology*, $4^{th}$ ed., John Wiley & Sons, vol. 16, pp. 539-541). The reaction may also be catalyzed by palladium. (ibid, Vol. 19, P. 368). The same catalysts will also promote the equation 5 reaction since it is the reverse of methanol synthesis.

Equation 4 is the classical method for preparing methyl mercaptan by alcohol substitution. It is known to be promoted by the use of a strong acid catalyst. (ibid, Vol. 24, p. 23) It is also catalyzed by thorium oxide. (Conant, J. B. and Blatt, A. H., *The Chemistry of Organic Compounds*, $3^{rd}$ ed., The MacMillan Co., New York 1947.) In conclusion, the preferred catalyst for the present invention is an intimate mixture of a methanol synthesis catalyst and a catalyst that promotes alcohol substitution.

Elevated reaction temperatures are required to achieve acceptable conversions. The less active methanol synthesis catalyst, namely, zinc-chromium oxide, requires a temperature in the range of 320° C. to 450° C. The more active catalyst with the composition copper-zinc-alumina is useful at a temperature as low as 210° C. Concerning the formation of methyl mercaptan, thorium oxide is reported to be effective at 350° C. Considering these inputs as guidelines, a range of 250° C. to 350° C. is recommended for the present invention.

Because of favorable thermodynamic data for the present invention, high pressures as used in methanol synthesis can be avoided. Near the upper temperature limit of 350° C., however, the conversion drops off. Under these circumstances, moderate pressures, up to about 10 atmospheres may be advantageous. Such limited pressure is favorable because there is a reduction in the volume of gases during the reaction.

Since the reaction of the present invention is exothermic, heat must be removed from the reactor in order to control the temperature of the reaction. This objective is easily achieved by using a shell and tube reactor design. Alternatively, a fluidized bed reactor might be considered.

Figure 2:
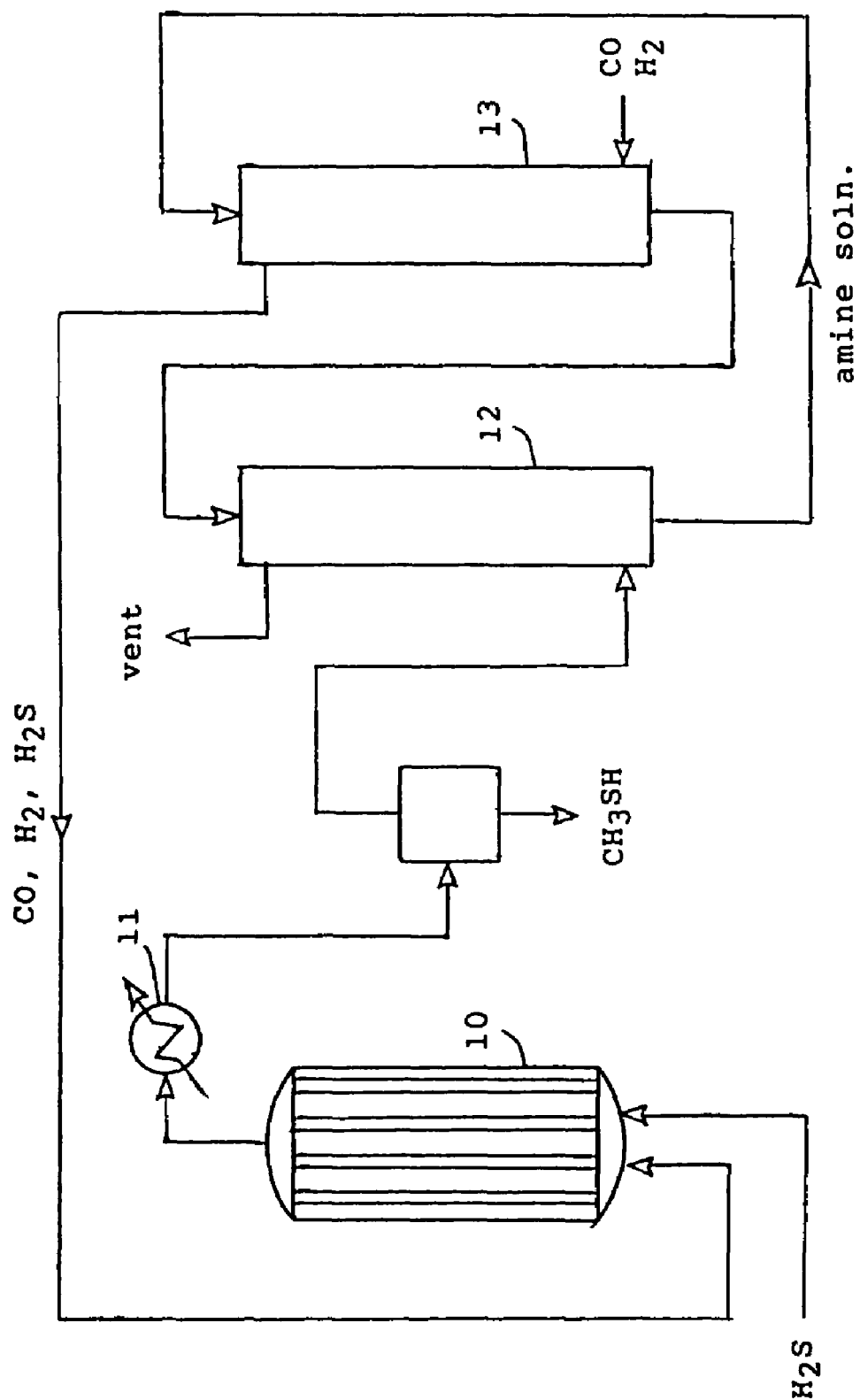
FIG. 2 is a schematic diagram of the process showing the major pieces of equipment. This flow sheet provides for the recovery of product and the recycle of any unreacted hydrogen sulfide.

The recovery of methyl mercaptan and the recycle of unreacted hydrogen sulfide are shown in FIG. 2. Exit gases from reactor 10 are cooled in heat exchanger 11. The boiling point of methyl mercaptan is 5.96° C. so that refrigeration is required. Noncondensed gases are sent to scrubber 12 where any unreacted hydrogen sulfide is absorbed in an alkanolamine stream. Inert gases from the scrubber are vented. The alkanolamine solution is pumped to stripper column 13 where hydrogen sulfide is recovered and recycled back to reactor 10.

The uses of methyl mercaptan are extensive. The compound undergoes numerous reactions of commercial interest. For example, methyl mercaptan can be used in the preparation of DL-motioning. If methyl mercaptan were available at a lower cost, it's applications could be expanded.

EXAMPLE

Engineering calculations were made to determine the conversion of raw materials when the process was operated under the following conditions: 2 mols of carbon monoxide mixed with 1 mol of hydrogen and 1 mol of hydrogen sulfide were fed to the reactor. The temperature of the reaction was maintained at 325° C. and the pressure was kept at 5 atmospheres. At equilibrium, 68.5% of the reactants were converted to methyl mercaptan and carbon dioxide in a single pass through the reactor.

What is claimed is:

1. A process for the manufacture of methyl mercaptan comprising the reaction of carbon monoxide, hydrogen, and hydrogen sulfide over a catalyst to provide, methyl mercaptan and carbon dioxide; wherein the catalyst is thorium oxide, and wherein the molar ratio of carbon monoxide to hydrogen to hydrogen sulfide in the feed is approximately 2:1:1.

2. A process of claim 1 Wherein the reaction is carried out at a temperature in the range of 250° C. to 350° C.

3. A process of claim 1 wherein the reaction is carried out at pressure in the range of 1 to 10 atmospheres.

* * * * *